United States Patent [19]

Kasper et al.

[11] Patent Number: 5,302,386
[45] Date of Patent: Apr. 12, 1994

[54] BACTERIAL ANTIGENS, ANTIBODIES, VACCINES AND METHODS OF MANUFACTURE

[75] Inventors: Dennis L. Kasper, Newton Center, Mass.; Harold J. Jennings, Gloucester, Canada; Nancy J. Levy, Newton Center; Michael R. Wessels, Brookline, both of Mass.

[73] Assignee: Brigham and Women's Hospital, Inc.

[21] Appl. No.: 982,023

[22] Filed: Nov. 24, 1992

Related U.S. Application Data

[63] Continuation of Ser. No. 701,595, May 13, 1991, abandoned, which is a continuation of Ser. No. 303,095, Jan. 27, 1989, abandoned, which is a continuation of Ser. No. 852,840, Apr. 16, 1986, abandoned.

[51] Int. Cl.[5] .................. A61K 39/385; A61K 39; A61K 09; C12P 19/04; C07K 17/02
[52] U.S. Cl. ........................... 424/92; 424/88; 424/85.8; 530/405; 530/411; 435/101; 435/207
[58] Field of Search ................ 530/411, 405; 424/88, 424/92, 85.8; 435/101, 207

[56] References Cited

U.S. PATENT DOCUMENTS

| | | | |
|---|---|---|---|
| 4,207,414 | 6/1980 | Kasper | 536/53 |
| 4,356,263 | 10/1982 | Kasper | 435/101 |
| 4,413,057 | 11/1983 | Carlo et al. | 435/101 |
| 4,591,552 | 5/1986 | Neurath | 435/7 |

OTHER PUBLICATIONS

Nakazawa, et al, J. Biol. Chem., 250(3):912–917 (1975).
Kitamikado, et al, J. Biol. Chem, 256(8):3906–3909 (1981).
Russell, et al., J. Immunol., 109(1):90–96 (1972).
Insel et al., J. Exp. Med., vol. 163, 1986, pp. 262–269.
Jennings et al., Canadian J. Biochem., vol. 58, 1980, pp. 112–120.
Jennings et al., Biochem., vol. 20, 1981, pp. 4511–4518.
Lancefield, J. Exp. Med., vol. 108, pp. 329–341 (1938).
Russell-Jones, J. Exper. Med., vol. 160, p. 1476 (1984).
Baker, "Group B Streptococcal Infections" in Advances in Internal Medicine, vol. 25, pp. 475–500 (1980).
Lancefield et al., J. Exp. Med., vol. 142, pp. 165–179 (1975).
Henrichsen et al., Int. J. of Systematic Bacteriol., vol. 34, p. 500 (1984).
Wilkinson et al., Infect. Immunol., vol. 4, pp. 596–604 (1971).
Bevanger et al., Acta Path. Microbiol. Scand. Sect. B, vol. 87, pp. 51–54 (1979).
Bevanger et al., Acta Path. Microbiol. Scand. Sect. B, vol. 89, pp. 205–209 (1981).
Insel and Andersen, J. Exp. Med., vol. 163, p. 262 (1986).

*Primary Examiner*—Kay K. Kim
*Attorney, Agent, or Firm*—Morgan & Finnegan

[57] ABSTRACT

Antigens and vaccines containing purified oligomers (1–50 units) of the repeating pentasaccharide unit of type III Group B Stretococcus (III GBS) polysaccharide capsule. Methods of making the antigen by recovering polysaccharide from cultured III GBS or medium and digesting the polysaccharide with a specific endo-β-galactosidase. Enzymatic cleavage of bacterial polysaccharide to make purified oligomers. A purified trypsin-resistant C surface protein, m.w. about 14,000 and vaccine. Passive immunization using the above vaccines. Immunoassays for GBS immunodeterminants or anti-GBS antibodies.

12 Claims, 1 Drawing Sheet

BACTERIAL ANTIGENS, ANTIBODIES, VACCINES AND METHODS OF MANUFACTURE

This invention was supported at least in part by grants from the National Institutes of Health and the Government has rights in the invention.

This application is a continuation of U.S. Ser. No. 07/701,595, filed on May 13, 1991, now abandoned, which is a continuation of U.S. Ser. No. 07/303,095, filed on Jan. 27, 1989, now abandoned, which is a continuation of U.S. Ser. No. 06/852,840, filed on Apr. 16, 1986, now abandoned.

BACKGROUND OF THE INVENTION

This invention relates to antigens having immunogenic determinants of Group B Streptococcus bacteria, to vaccines protecting against those bacteria, to methods of making such vaccines, and to methods of preparing oligosaccharides from bacterial polysaccharides. As used in this application, the term Group B Streptococcus (or GBS) bacteria is used as understood by those in the field, particularly with reference to Lancefield, *J. Exp. Med.* 108:329–341 (1938) and subsequent work further characterizing Group B serotypes, e.g. Russell-Jones, *J. Exper. Med.* 160:1476 (1984). The term specifically includes bacteria taxonomically designated *Streptococcus agalactiae*.

GBS are a recognized etiological agent for bacteremia and/or meningitis in infants, and for infections in adults. Baker, "Group B Streptococcal Infections" in *Advances in Internal Medicine,* 25:475–500 (1980). Accordingly, it is important to develop rapid and definitive assays for diagnosis of GBS infection, and methods of generating protection against GBS, particularly in infants and compromised individuals.

The GBS capsular polysaccharides are known to be important to GBS virulence and immunity. Baker, cited above. Moreover, the recognized GBS types and subtypes have chemically related but antigenically distinct capsular polysaccharides having a repeating structure composed of galactose, glucose, N-acetyl glucosamine, and N-acetyl-neuraminic (sialic) acid. Baker, cited above. Type III GBS capsular polysaccharide is composed of a backbone made up of repeating branched pentasaccharide units. Jennings et al., Canadian J. Biochem. 58:112–120 (1980).

One study of type III GBS polysaccharides suggests that the natural immunodeterminant site is located at the side chain-backbone junction. Jennings et al., Biochemistry 20:4511–4518 (1980). The presence of the side chain terminal N-acetyl-neuraminic acid residues reportedly was critical for immunodeterminant expression.

Studies of GBS protein immunogenicity are also reported. Lancefield et al., *J. Exp. Med.* 142:165–179 (1975) report that the so-called C proteins of GBS are capable of inducing protective antibodies when present as an immunogen on a whole organism. The nomenclature "C proteins" is used as defined by Henrickson et al., J. System Bacteriol. 34:500 (1984), and the term includes proteins formerly designated Ibc proteins.

Molecular studies of C proteins have shown that these substances constitute a complex group of proteins of variable molecular weight. Wilkinson et al., Infect. Immunol. 4:596–604 (1971); Bevanger et al., Acta Path. Microbiol. Scand. Sect. B, 87:51–54 (1971); Russell-Jones et al., J. Exp. Med. 160:1476–1484 (1984). Bevanger et al., Acta Path. Microbiol. Scand. Sect. B, 89:205–209 (1981).

Wilkinson et al. disclose that hot acid extracts of whole type Ic GBS yields 13 proteins of varying molecular size (determined by polyacrylamide gel electrophoresis) having serological reactivity in agar gel against type Ic antisera. Bevanger et al. (1979) disclose GBS acid extract containing nine trypsin sensitive proteins and five trypsin resistant but pepsin sensitive proteins. Bevanger et al. (1981) disclose immunogenicity of partially purified acid extracted proteins. Russell-Jones et al. disclose extracts containing up to 30 proteins varying in molecular weight from 20,000 to 130,000, the 130 kd protein being predominant. Russell-Jones et al. also report that multiple proteins reacted by immuno (Western) blot to a single monoclonal antibody, suggesting that some proteins were breakdown products of others. Using another monoclonal antibody, the 130,000 MW proteins and 12 other proteins spaced between 10,000 and 120,000 MW appeared to share a common epitope.

Insel and Andersen, *J. Exp. Med.* 163:262 (1986) disclose conjugating *Haemoplilus influenzae* capsular polysaccharide to a protein carrier in an effort to convert the capsule to a more thymus-dependent immunogen.

SUMMARY OF THE INVENTION

We have discovered that oligomers of the repeating pentasaccharide unit of the type III Group B Streptococcus (III-GBS) polysaccharide capsule (and even the single unit alone) are antigenic. Antigens containing the unit, particularly antigens containing repeated units, can be used as a component of a III-GBS vaccine. Accordingly, one aspect of the invention features an antigen capable of raising an antibody selectively immunoreactive with type III Group B Streptococcus (III GBS) bacteria, and comprising a purified oligosaccharide having the following formula:

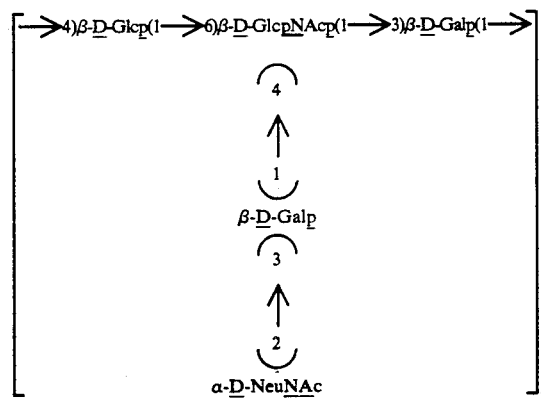

in which n=1–50, GlcNAcp represents N-acetyl glucosamine (in the pyranose form), Galp represents galactose (in the pyranose form), Glcp represents glucose (in the pyranose form), and α-D-NeuNAc represents N-acetyl neuraminic (sialic) acid.

"Purified" means substantially separated from the various protein, lipid, and carbohydrate components that naturally occur with the oligosaccharide. In particular, purified oligosaccharide is substantially free from intact III GBS polysaccharide capsule, or fragments of it having a molecular weight above 100,000. Whatever traces of foreign components are in the purified oligosaccharide do not interfere with the use of the purified material in a vaccine or as an antigen. The term "purified" is not intended to exclude synthetic oligosaccharide preparations retaining artifacts of their synthesis; nor is the term meant to exclude preparations that include some impurities, so long as the preparation exhibits reproducible oligosaccharide characterization data, for example molecular weight, sugar residue content, sugar linkages, chromatographic response, and immunogenic behavior.

In a second aspect, the invention features a vaccine capable of eliciting protection against III GBS, comprising a pharmaceutically acceptable vehicle and the above described antigen, optionally conjugated to a carrier.

A third aspect of the invention features a method of making the above-described antigen by: 1) culturing III-GBS bacteria in a suitable medium; 2) recovering polysaccharide in the medium or from the bacteria cells; 3) digesting the polysaccharide with an endo-$\beta$-galactosidase specific for cleaving the linkage $S_1(1\rightarrow3)$-$\beta$-gal$(1\rightarrow4)S_2$, $S_1$ and $S_2$ are independently selected from glucose, glucosamine, or N-acetyl glucosamine; and 5) recovering the oligosaccharide antigen from the medium or from the bacteria. Optionally, the oligosaccharide is conjugated to a carrier as described below.

In preferred embodiments of any of the first three aspects, the oligosaccharide antigen is produced by enzymatic hydrolysis of III GBS capsular polysaccharide using an endo-$\beta$-galactosidase specific for the above-described linkage. One such endo-$\beta$-galactosidase is found in *Flavobacterium keratolyticus*. Also preferably, the oligosaccharide is covalently bound (e.g., via a secondary amine link) to a carrier such as a protein, particularly a bacterial toxoid or a bacterial surface protein, comprising a bacterial immunodeterminant site.

In a fourth aspect, the invention more generally features enzymatic cleavage of a bacterial polysaccharide having the above-described linkage, in a method of making a purified oligosaccharide; specifically a bacteria having a surface polysaccharide (e.g a polysaccharide capsule or membrane) is cultured, and the polysaccharide is extracted, after which it is digested with the above-described enzymes and the oligosaccharide is recovered. Preferably the bacteria is gram positive, e.g., type III GBS; alternatively the bacteria can be a species having a surface capsule polysaccharide, such as type 14 *Streptococcus pneumoniae*, e.g., ATCC No. 6314.

In a fifth aspect, the invention features a substantially purified trypsin-resistant C surface protein of type Ia/c Group B Streptococcus, the protein having a molecular weight about 14,000, and being non-cross-immunoreactive with Group B Streptococcus bacterial polysaccharides, yet cross-immunogenic with type Ia/c GBS. In other aspects, the above described protein is used in a vaccine that elicits protection against type Ia/c (and type Ib/c) GBS, which vaccine comprises the protein (optionally conjugated to an oligosaccharide such as the III GBS oligosaccharide described above) and a pharmaceutically acceptable carrier. The resulting conjugate provides broad protection against GBS, in that it protects against III GBS and against GBS having C protein.

In yet another aspect, the invention features a gamma globulin fraction capable of passive protection against GBS, the fraction being produced by immunizing a mammal with one of the above-described vaccines. The fraction is then administered to an individual to provide protection against GBS infection or to treat on-going infection.

Finally, the invention features a method of assaying a sample for anti GBS antibody by adding to the sample the oligosaccharide or protein antigen described above, and then detecting the formation of an immunocomplex; alternatively a sample is assayed for the presence of a GBS immunodeterminant by raising an antibody to the oligosaccharide or protein antigen, adding the antibody to the sample, and detecting the formation of an immunocomplex.

The enzymatic selective hydrolysis of the backbone glycosidic bonds is superior to simple acid hydrolysis, because the latter technique results in the loss of the side chain sialic acid residues, and cleaves bonds non-selectively, yielding a heterogeneous mixture of reduced immunogenicity. In contrast, enzymatic digestion preserves the sialic acid residues and produces backbone cleavage only at the gal-$\beta$1-4-glc bonds, which occur once per backbone repeating unit.

Other features and advantages of the invention will be apparent from the following description of the preferred embodiments and from the claims.

DESCRIPTION OF THE PREFERRED EMBODIMENTS

Figure 1:
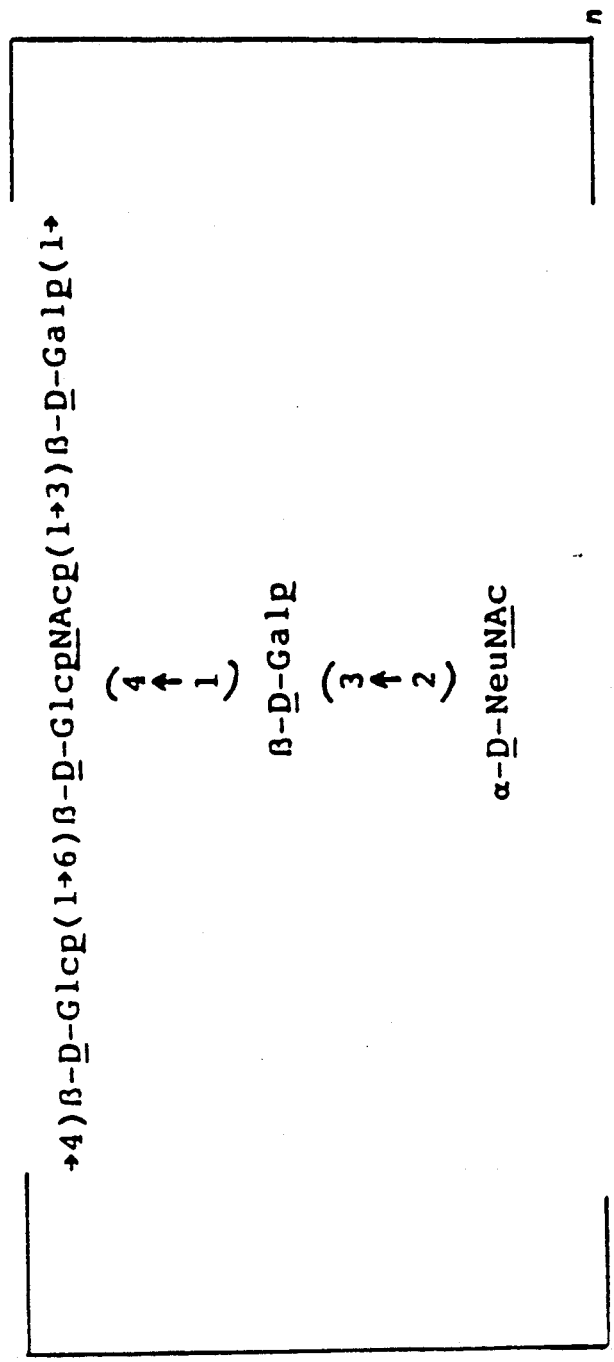

We now describe preferred embodiments of the invention, first briefly describing the drawing.

I. Drawing

FIG. 1 is a diagram of a repeating pentasaccharide of the III GBS capsular polysaccharide.

II. Type III GBS Antigen And Vaccine

A. Oligosaccharide

The specific pentasaccharide described above is obtained by culturing type III GBS and extracting the polysaccharide capsule from the supernatant broth or from the bacterial cells by the general method of Jennings et al., *Canadian J. Biochem.* 58:112–120 (1980). The polysaccharide extract is digested by an endo-$\beta$-galactosidase that specifically cleaves the structure $S_1(1\rightarrow3)\beta gal(1\rightarrow4)\beta S_2$, where $S_1$ and $S_2$ are independently selected from glucose, glucosamine, or N-acetyl glucosamine. The above structure occurs once per repeating unit of the III GBS polysaccharide capsule, and the resulting cleavage products are oligosaccharides having one or more of the above-described pentasaccharide repeating units.

The enzyme is obtained from bacteria known to produce an enzyme catalyzing the requisite specific cleavage. One such preferred bacteria is *Flavobacterium keratolyticus*. Another bacterium thought to produce an enzyme with the requisite specific activity is *Bacteroides fragilis*. Kitamikado et al., cited below, report that the requisite endo-$\beta$-galactosidase activity is also present in *Escherichia freundii*, Pseudomonas sp., and Cocobacillus sp. when induced on keratan sulfate. See Nakagawa et al. *J. Biol. Chem.* 250:912–917; and Hirano et al. Connect. Tissue Res. 2:1–10. A suitable *F. keratolyticus* can be obtained from the Institute of Fermentation (IFO) Osaka, Japan, under the designation IFO #14087. A suitable general procedure for preparing endo-$\beta$-galactosidase is given by Kitamikado et al., *J. Biol. Chem.* 256:3906–3909 (1981).

The extracted III GBS polysaccharide capsule prepared as described above is added to a buffered enzyme preparation, and incubated (e.g., 37° C, 48 hrs.). After digestion, the oligosaccharides are separated by molecular weight by gel filtration chromatography, e.g., Sephadex G75 (Pharmacia), and purified by anion exchange chromatography, e.g., anion exchange high performance liquid chromatography (HPLC), Mono Q (Pharmacia), or QAE Sephadex (Pharmacia).

A purified oligosaccharide comprising between about 1 and 50 (and most preferably between about 2 and 30 pentasaccharide units) is selected from chromatographic group and then conjugated to a protein for use in a vaccine. The protein may be an inactive carrier, or it can be selected to provide some protection in its own right, particularly protection that complements the protection induced by the oligosaccharide, for example, by inducing protection against other types of GBS or other bacteria. The non-toxic diphtheria toxin analog, CRM 197, may be used as described by Insel et al. (1986) J. Exp. Med. 163:262 and Andersen et al. J. Clin. Invest. 76:52 (1985). Other toxoids that can be used include tetanus or standard diphtheria toxoids available from the Massachusetts State Laboratory, South Street, Jamaica Plain, Mass.

Protein-oligosaccharide conjugation is achieved by a coupling reaction, such as the general method of Swartz and Gray, Arch. Bioch. Biophys. (1977) 181:542, which couples a reducing sugar directly to a protein. Oligosaccharide fragments produced by deamination can be directly linked via cyanoborhydride to the carrier protein. In the case of III GBS, a secondary amine is formed by bonding between a nitrogen on the protein and an aldehyde group on 2,5-anhydromannose formed by deamination of the oligosaccharide. This aldehyde is available for direct coupling using cyanoborhydride.

The resulting oligosaccharide-protein conjugate is suspended in pyrogen-free saline or any other physiologically acceptable non-toxic vehicle or medium, which may contain any conventional stabilizers or other additives as desired. The concentration of antigen is not critical and may be varied over a wide range, but for many purposes a range of 10-1000 μg/ml is convenient and suitable. In this form it is stable during prolonged storage at 4° C. and is sterile, non-toxic, and non-pyrogenic when subjected to animal tests as prescribed by Food and Drug Administration Regulations (Title 21, Sec. 610.11-610.13). Suitable volumes (e.g. about 0.5 ml) of the above-described saline suspension are administered (e.g. by subcutaneous injection) to induce III GBS protection.

The invention also features a method of passive immunization, used particularly for infants or compromised adults, by injecting the oligosaccharide-protein conjugate vaccine into a human to raise antibodies thereto in high titer, separating the antiserum from the blood of the human, and fractionating the antiserum to produce a gamma globulin fraction containing the antibodies, which can be used for passive immunization. This method of establishing donors for passive immunization is useful because, although occasional non-immunized human adults have very high levels of type-specific GBS antibody in their sera, it would be necessary to screen very large populations to select those individuals whose plasma could be pooled to make sufficiently high titered globulin fractions to be useful for passive immunizations. Several lots of pooled human gamma globulin from non-immunized adults have been assayed for anti-Types Ia and Ic, anti-Type II, and anti-Type III polysaccharide antibody and have been found to contain only 5-20 μg/ml of serum. Immunizations by intravenous injection of such low titer globulins would require prohibitively large doses with attendant risk of adverse reactions.

For passive immunization, pools of human sera from selected individuals vaccinated with the above-described conjugated polysaccharide vaccine can be concentrated and fractionated by conventional procedures to provide a globulin fraction containing most of the type-specific antibody and of sufficiently high activity so that the hyperimmune globulin is effective in small doses of 0.3-1 ml, preferably about 0.5 ml, when administered in a suitable physiologically acceptable carrier such as normal saline either intravenously or intramuscularly. The concentration of the globulin in the carrier may be from 5 to 20% y weight. The hyperimmune globulin can be administered either to pregnant women prior to delivery, to neonates, or to immunologically compromised individuals, to provide passive immunization or therapy.

III. Oligosaccharide Antibodies

Oligosaccharides generally can be recovered from endo-β-galactosidase digestion of bacterial polysaccharides. The above description concerns III GBS oligosaccharides and their use in vaccines, however, the oligosaccharides also can be used to elicit antibody in experimental mammals, e.g., by challenging the mammal, e.g. by injecting the oligosaccharide protein conjugates, and recovering the resulting antibody. Also, monoclonal antibodies can be generated by standard techniques. The resulting antibodies are useful, e.g. in immunoassays for GBS, or III GBS in particular. For example, the antibody to the oligosaccharide can be used for immunoassays such as competitive or sandwich immunoassays known in the field.

The following examples illustrate the oligosaccharide antigen, the method of isolating the oligosaccharide, the vaccine, and the method of passive immunization.

EXAMPLE 1

Preparation of endo-β-galactosidase

*F. keratolyticus* is cultured overnight and used to inoculate a modified trypticase peptone broth (3% trypticase peptone from BBL Microbiology Systems, Cockeysville, Md.); 0.1% yeast extract (Difco Laboratories, Detroit Mich.); 0.2% NaCl, pH 7.0. The broth is incubated for 18 hours (Biolafitte fermentor, Lafitte, France), while controlling aeration (15 l/min), stirring (150 rpm), temperature (25° C.), and pH (7.0). Bacteria are removed by centrifugation and the supernatant concentrated (Pellicon Cassette System, Millipore Corp., Bedford Mass.). Solid $(NH_4)_2SO_4$ is added to 75% saturation and the solution is allowed to stand overnight at 4° C.

Precipitate is removed by centrifugation and dissolved in 10 mm sodium acetate, 0.2M NaCl, pH6.0. The solution is loaded onto a 5×90 cm Sephadex G-100 column (Pharmacia Fine Chemicals, Piscataway N.J.) and eluted with the same buffer at 40 ml/hr, 4° C. Active fractions are identified by assaying for endo-β-galactosidase activity and then pooled. Specifically, the fractions are incubated with bovine cornea keratan sulfate (Sigma Chemical Co., St. Louis Mo.) overnight at 37° C. Production of reducing sugar is measured by the general method of Park and Johnson, *J. Biol. Chem.* 181:149-151 (1949).

Pooled active fractions are dialyzed, lyophilized, and dissolved in buffer (50 mM sodium acetate, 2 mM $CaCl_2$, pH 6.0). The buffered enzyme preparation is loaded onto a 2.5×14 cm column containing DEAE Sephacel (Pharmacia) in the top half and BioRex 70 (BioRad Laboratories, Rockville Center N.Y.) in the bottom half. The enzyme elutes with 250 ml of the above buffer. Residual bound protein is eluted with 1.0M NaCl, and active pooled fractions are dialyzed against 10 mM sodium acetate, 2 mM $CaCl_2$, PH 7.0, and lyophilized.

EXAMPLE 2

Polysaccharide Digestion

GBS type III polysaccharide is extracted by the general technique of Jennings (1980) cited above. The lyophilized endo-$\beta$-galactosidase preparation from one DEAE Sephacel/BioRex 70 column run is dissolved in 10 ml 10 mM sodium acetate, 2 mM calcium chloride, pH 7.0 and dialyzed against 2 liters of the same buffer overnight at 4° C. with one bath exchange. Twenty mg of purified type III GBS capsular polysaccharide is added to the enzyme preparation. The mixture is filter sterilized, and incubated at 37° C. for 48 h, with stirring.

EXAMPLE 3

Oligosaccharide Purification And Characterization

After digestion, oligosaccharides are separated into large versus small molecular weight pools by dialysis against water through a 12,000–14,000 dalton pore size membrane (Spectrum Medical Industries, Los Angeles, Calif.). Oligosaccharides corresponding to one (pentasaccharide) and two (decasaccharide) repeating units are purified by anion exchange chromatography. Small amounts of oligosaccharides (1 mg or less) can be purified by anion exchange high performance liquid chromatography (HPLC). Five hundred µg of digestion mixture (small molecular weight pool) are loaded on a 5×50 mm Mono Q column (Pharmacia) and one and two repeating unit oligosaccharides are eluted isocratically with 20 mM Tris HCl buffer, pH 7.2. Larger oligosaccharides can be eluted with higher salt concentrations. For purification of large amounts of oligosaccharides, a 1.2×10 cm column filled with QAE Sephadex A50 (Pharmacia) is used. Samples of 2–8 mg are loaded onto this column in a starting buffer of 20 mM N-methyl diethanolamine acetate, pH 9.6. The column is washed with 30 ml starting buffer at 1 ml/min, then the single repeating unit oligosaccharide is eluted with 50 ml of starting buffer containing 15 mM Na acetate. Two ml fractions are collected, neutralized with 1M acetic acid, and analyzed by thin layer chromatography (TLC). Fractions containing the single repeating unit oligosaccharide are pooled, lyophilized, dissolved in 2 ml water, and desalted on a 1.6×25 cm column containing Sephadex G15 (Pharmacia).

The major digestion product corresponds to a band migrating between tetrasaccharide and decasaccharide standards, and has a molecular size compatible with that predicted for the pentasaccharide unit of FIG. 1. Diphenylamine and resorcinol staining of this band is consistent with a sialylated sugar. Methylation analysis confirms that structure is a complete pentasaccharide repeating unit.

One and two repeating-unit oligosaccharides are purified by anion exchange chromatography. Anion exchange HPLC is a quick and convenient method for purifying small amounts of oligosaccharides (1–2 mg or less). The single repeating unit oligosaccharide elutes in the void volume, while the two repeating unit oligosaccharide elutes later in the isocratic phase. Larger oligosaccharides or native polysaccharide, are retained in the isocratic phase, but are readily eluted from this column with 0.5M sodium chloride. This method can be used to purify tritiated one and two repeating unit oligosaccharides for use in radioantibody binding assay (RABA) studies. See Schifferle (1985) J. Immunology 135:4164. For purification of larger amounts of single repeating unit oligosaccharide, an open anion exchange column can be used to provide a larger binding capacity. Using this QAE Sephadex A50 column, the single repeating unit, as well as larger oligosaccharides are retained in the starting buffer. The single repeating unit is eluted, free of larger oligosaccharides, with the starting buffer containing 15 mM sodium acetate. Larger oligosaccharides remain bound, and can be eluted with increased salt concentration. From digestion of 20 mg of type III native polysaccharide, 6 mg of purified single repeating unit oligosaccharide are obtained. The oligosaccharide corresponding to a minor band migrating just distal to the single repeating unit on TLC is also retained somewhat more avidly by the anion exchange column. Although complete separation is not achieved with preparative runs, the single repeating unit oligosaccharide purified in this manner is estimated to be 95% pure by TLC and methylation analysis. Larger oligosaccharides are also fractionated by chromatography, e.g., a Sephadex G75 column.

EXAMPLE 4

Binding Assay For Oligosaccharide

The chromatogram binding assay is used to examine directly the ability of the oligosaccharide bands visualized by TLC to bind antibody directed against the active polysaccharide. Antibody binding to the single repeating unit band is clearly evident. Although the assay is not quantitative, it is clear from the relative intensities of the bands on the autoradiograph that the native polysaccharide binds antibody more efficiently. This assay is highly specific for native type III polysaccharide—cross reactions are not seen with the desialylated core polysaccharide, with the group B polysaccharide, nor with capsular polysaccharides from other GBS serotypes.

The oligosaccharide antigen described above is then conjugated to a protein as described above, and suspended in pyrogen-free saline solution, as described above, to form a vaccine.

The single repeating pentasaccharide (FIG. 1) is weakly antigenic using radioantibody binding assay inhibition TLC binding assay, and direct radioantibody binding assay. Increasing oligosaccharide size or two repeating units results in an eight-fold increase in antigen binding. Most preferably, the immunogen includes 2–50 units.

IV. GBS Protein Antigen

An antigenic GBS C protein is isolated from type Ic GBS culture supernatants as illustrated by the following example. The protein is immunologically reactive with antisera (e.g., mouse antisera) to a P10 GBS protein fraction, i.e., a fraction including proteins of MW between 10,000 and 30,000. The purified protein elicits rabbit antisera that protect mice against challenge with type Ib GBS. This protective ability is not affected by incubations with GBS polysaccharides.

EXAMPLE 5

Production and purification of protein antigens

Type Ia/c GBS (e.g. Channing Laboratory Strain A909 Rockefeller University N.Y., N.Y., ATCC 27591) are cultured into late log phase in a dialysate of Todd Hewett Broth (THB, Difco Laboratories, Detroit, Mich.), and then resuspended in 0.3% formalin in 0.15M sodium phosphate buffer (pH 7.4), by the general method of Levy et al. J. Infect Dis. 149:851-868 (1984).

A one liter log phase culture of type Ic is added to 15 liters of the dialysate of THB (dialyzed on an exclusion membrane of 10,000 MW), supplemented with 10% glucose, and grown into late log phase maintaining neutral pH by titration in a fermentor (Biolafitte Model BL 20.2, LSL Biolafitte Inc., Princeton, N.J.). After removal of the bacteria by pelleting at 10,000 g, the supernatant is concentrated to 100 ml on a Pellicon apparatus (Millipore Corp., Bedford, Mass.) containing a 10,000 MW exclusion membrane, dialyzed against $H_2O$ extensively and frozen at $-20°$ C.

The culture supernatant is separated by approximate molecular size using ultrafiltration. Two fractions are obtained, one retained by a PM30 membrane (P30; greater than 30,000 MW), and another retained by a PM10 membrane but not retained by a PM30 (P10; greater than 10,000 MW and less than 30,000 MW). The P10 is dialyzed against 0.05M sodium phosphate buffer, pH 7.4 with 0.15M NaCl and fractionated on a Sephadex G-75 column (1.6×82 cm) (Pharmacia). The protein content of fractions is monitored by absorption at 750 nm in the Lowry assay, J. Biol. Chem, 193:265-275 (1951).

EXAMPLE 6

SDS-PAGE and Western blot

Samples are analyzed by SDS-PAGE following the method of Laemmli, Nature 227:680-684(1970). Gradient gels either 5-15% or 10-20% are employed depending on the molecular weight of the proteins. Samples for electrophoresis are diluted in a buffer containing 0.1M Tris, pH 8, 1% SDS, 4M urea and 60 mM iodoacetamide as final concentration. When reduction of the samples is required, 50 mM dithiothreiotol is included in the buffer. One hundred μl samples containing 100 μg protein are placed into each well. After electrophoresis the proteins are visualized by Coomassie brilliant blue stain.

To identify immunologically reactive antigens, Western blot is used. Proteins are first subjected to electrophoresis and the SDS-PAGE gel washed in Buffer A composed of 0.02M Tris buffer, pH 8.5 with 0.15M glycine and 20% methanol. The proteins are transferred to nitrocellulose sheets (Schleicher and Schuell, Keene, N.H.) by electrophoresis (150 mA, 20 h) in Buffer A and washed in 0.01M Tris buffer, pH 7.4 with 0.5M NaCl and 0.1% Brig 58 (Buffer B). The sheet is then incubated with antiserum for 2 h at 22° C. and washed in Buffer B. After incubation with $^{125}I$-protein A for 30 min at 22° C., the sheet is washed in Buffer B, blotted dry and exposed to Kodak XAR 5 film.

EXAMPLE 7

Mouse protection studies

Male outbred CD-1 mice weighing 22-24 gr are obtained from Charles River Breeding Laboratories (Wilmington, Mass.). Sera obtained from the mice contained no detectable antibody to type Ia/c GBS polysaccharide antigen as tested by RABA. Each experimental group contained between 5 and 10 animals. For mouse protection studies, mice are injected IP with 1 ml mouse or rabbit antiserum and 24 h later challenged IP with $1 \times 10^6$ CFU of type Ib/c GBS. Preimmune rabbit or mouse serum is used as the control. Mice are examined every 24 h and the number of surviving mice is calculated 48 h after bacterial challenge.

For absorption of protective antibodies from antisera, GBS polysaccharides or protein fractions in concentrations of 1 mg per ml are used. One ml of antiserum and one ml of polysaccharide or protein is incubated for 2 h at 37° C. and then overnight at 4° C. The mixture is then pelleted at 13,000 g for 3 min and the supernatant was diluted in 0.15M NaCl for protection studies.

After partial purification by column chromatography, the 14,000 MW protein was reisolated from preparative SDS-PAGE gel and used to elicit antiserum in a rabbit. In mouse protection studies this rabbit antiserum protected mice (89%) against Ia/c GBS challenge.

To investigate whether the P10 fraction could elicit mouse protective antibodies against a heterologous GBS strain, mice were immunized with the type Ia/c P10 fraction. The post immunization antisera were then pooled and examined for its capacity to protect mice against challenge with type Ib GBS. Mice were injected IP with various dilutions of pooled mouse antisera to the P10 fraction followed 24 h later by challenge with the type Ib/c strain. The protective capacity of the sera begins to dilute out at a 1:80 dilution of the sera. Therefore the sera were used at an optimal dilution of 1:40 for these experiments. In mouse protection studies the immune sera protected mice against challenge with the type Ib strain ($P<0.001$) compared with the normal mouse sera at the same dilution. This pooled sera contained no detectable antibody to the type Ia polysaccharide as measured in the RABA. Furthermore absorption of the pooled antisera with the type Ia or Ib polysaccharide did not significantly alter the protective level. The protective efficacy of mouse antisera to P10 fraction from type Ic contained non-capsular antigens which elicited antibody in mice which passively protected mice against challenge with the type Ib GBS.

Specifically, rabbit antiserum to the SDS-PAGE eluted 14,000 MW protein from type Ic GBS was next used in mouse protection studies. Mice were injected with antiserum IP and challenged 24 hours later with type Ib GBS. The antiserum elicited to the SDS-PAGE eluted 14,000 MW protein was protective in mice at dilutions of 1:5 and 1:10. The difference between the normal rabbit serum and the antiserum elicited to the SDS-PAGE eluted 14,000 MW protein was significant.

Other embodiments are within the following claims.

We claim:

1. An immunogenic substance comprising a purified oligosaccharide hapten and a protein carrier conjugated with said oligosaccharide hapten, said oligosaccharide hapten consisting essentially of from 1-50 monomer units of the type III group B Streptococcus polysaccharide capsule, said monomer units having the following chemical formula:

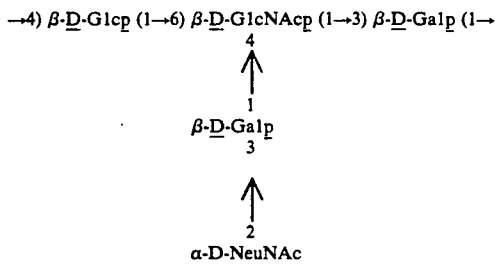

in which GlcNAcp represents N-acetyl glucosamine in the pyranose form, Galp represents galactose in the puranose form, Glcp represents glucose in the pyranose form, and α-D-NeuNAc represents N-acetyl neuraminic (sialic) acid; said oligosaccharide hapten being prepared by a) culturing a type III group B Streptococcus bacterium in a medium;

b) recovering polysaccharide capsule in said medium or bacterial cells, said polysaccharide capsule having a backbone and side chains;

c) digesting said polysaccharide with an endo-β-galactosidase specific for cleaving one linkage on the backbone of said III GBS polysaccharide without cleaving side chain linkages of said III GBS polysaccharide and without cleaving other backbone linkages of said III GBS polysaccharide; and d) recovering said oligosaccharide hapten.

2. The immunogenic substance of claim 1 wherein said protein is covalently bound to said oligosaccharide by a secondary amine function.

3. The immunogenic substance of claim 1 wherein said protein comprises a bacterial surface protein.

4. The immunogenic substance of claim 1 wherein said protein comprises a bacterial toxoid.

5. A method of making the immunogenic substance of claim 1 wherein the oligosaccharide hapten is prepared by a) culturing a type III group B Streptococcus bacterium in a medium;

b) recovering polysaccharide capsule in said medium or bacterial cells, said polysaccharide capsule having a backbone and side chains;

c) digesting said polysaccharide with an endo-β-galactosidase specific for cleaving one linkage on the backbone of said III GBS polysaccharide without cleaving side chain linkages of III GBS polysaccharide and without cleaving other backbone linkages of said III GBS polysaccharide; and d) recovering said oligosaccharide hapten.

6. The method of claim 5 wherein said endo-β-galactosidase is obtained from *Flavobacterium keratotylicus*.

7. The method of claim 5 wherein said method comprises covalently binding said oligosaccharide to a protein.

8. The method of claim 7 wherein said protein is covalently bound to said oligosaccharide by a secondary amine function.

9. The method of claim 7 wherein said protein comprises a bacterial surface protein.

10. The method of claim 7 wherein said protein comprises a bacterial toxoid.

11. The method of claim 5 further comprising conjugating said oligosaccharide to a carrier.

12. A vaccine that elicits immunological protection against type III group B Streptococcus bacteria, said vaccine comprising a pharmaceutically acceptable vehicle and the immunogenic substance of claim 1.

* * * * *